(12) United States Patent
Uno et al.

(10) Patent No.: US 7,888,517 B2
(45) Date of Patent: Feb. 15, 2011

(54) PROCESS FOR PRODUCTION OF GLYCIDOL

(75) Inventors: Mitsuru Uno, Wakayama (JP); Munehisa Okutsu, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/304,740

(22) PCT Filed: Jun. 14, 2007

(86) PCT No.: PCT/JP2007/061992

§ 371 (c)(1),
(2), (4) Date: May 11, 2009

(87) PCT Pub. No.: WO2007/145278

PCT Pub. Date: Dec. 21, 2007

(65) Prior Publication Data

US 2009/0318718 A1      Dec. 24, 2009

(30) Foreign Application Priority Data

Jun. 15, 2006    (JP) .............................. 2006-165733

(51) Int. Cl.
*C07D 317/12*    (2006.01)

(52) U.S. Cl. ...................................... 549/229; 549/518

(58) Field of Classification Search ................. 549/229, 549/518

See application file for complete search history.

(56) References Cited

U.S. PATENT DOCUMENTS

| 2,856,413 | A | 10/1958 | Malkemus et al. |
| 5,359,094 | A | 10/1994 | Teles et al. |
| 6,025,504 | A | 2/2000 | Claude et al. |
| 6,495,703 | B1 | 12/2002 | Okutsu et al. |

FOREIGN PATENT DOCUMENTS

| EP | 0 582 201 A2 | 2/1994 |
| EP | 0 955 298 A1 | 11/1999 |
| EP | 1 156 042 A1 | 11/2001 |
| JP | 6-157509 A | 6/1994 |
| JP | 2000-247967 A | 9/2000 |

*Primary Examiner*—Janet L Andres
*Assistant Examiner*—David E Gallis
(74) *Attorney, Agent, or Firm*—Birch, Stewart, Kolasch & Birch, LLP

(57) ABSTRACT

The present invention relates to a process for producing glycidol from glycerol carbonate as a raw material with a high yield. The process for producing glycidol according to the present invention includes the steps of (1) reducing a content of a salt having a weak acidity in glycerol carbonate to 1500 ppm by mass or less; and (2) obtaining the glycidol from the glycerol carbonate.

6 Claims, No Drawings

PROCESS FOR PRODUCTION OF GLYCIDOL

TECHNICAL FIELD

The present invention relates to a process for producing glycidol from glycerol carbonate.

BACKGROUND ART

It is known that the reaction for producing glycidol from glycerol carbonate is desirably carried out in the presence of a neutral salt such as sodium sulfate, although the reaction proceeds by thermal decarboxylation of glycerol carbonate even without using any catalyst (for example, refer to Patent Documents 1 and 2).

On the other hand, it is also known that glycerol carbonate is produced by not only a method using phosgene but also a method of subjecting dimethyl carbonate, ethylene carbonate, propylene carbonate or the like and glycerol to exchange reaction therebetween, a method of obtaining the glycerol carbonate from glycerol and urea, etc. Among these methods, the method using glycerol and urea allows the glycerol carbonate to be produced in a facilitated manner at low costs. In this method, although the reaction proceeds even under a catalyst-free condition, it is known that the glycerol carbonate is produced with a high yield when using a Lewis acid such as zinc sulfate and magnesium sulfate as a catalyst in the reaction (for example, refer to Patent Document 3).

Patent Document 1: U.S. Pat. No. 2,856,413
Patent Document 2: JP 6-157509A
Patent Document 3: EP 0955298A

DISCLOSURE OF THE INVENTION

Problem to be Solved by the Invention

However, almost all of attempts for producing glycidol from the crude glycerol carbonate as a raw material obtained using such an acid catalyst by the conventionally known methods have resulted in extremely low yield of glycidol as aimed.

The present invention relates to a process for production of glycidol in which the glycidol can be produced from the crude glycerol carbonate as a raw material with a high yield.

Means for Solving Problems

Thus, the present invention relates to a process for producing glycidol, including the steps of:

(1) reducing a content of a salt having a weak acidity in glycerol carbonate to 1500 ppm by mass or less; and (2) obtaining the glycidol from the glycerol carbonate.

Effect of the Invention

According to the production process of the present invention, even when producing glycidol, for example, by using glycerol carbonate obtained from glycerol and urea as a raw material, the content of a salt having a weak acidity in the glycerol carbonate is reduced, thereby enabling the aimed glycidol to be produced with a high yield.

BEST MODE FOR CARRYING OUT THE INVENTION

The present invention is described in detail below.

The present invention relates to a process for producing glycidol, including the steps of (1) reducing a content of a salt having a weak acidity in glycerol carbonate to 1500 ppm by mass or less; and (2) obtaining the glycidol from the glycerol carbonate. In the following, the respective steps of the process are explained.

Step (1)

In the process of the present invention, from the viewpoint of enhancing a yield of the obtained glycidol when using glycerol carbonate as a raw material therefor, there is provided the step (1) of reducing a content of a salt having a weak acidity which exists in the glycerol carbonate.

The salt having a weak acidity as used herein means such a salt formed between a basic ion and an acidic ion exhibiting a high dissociation ability. More specifically, the salt having a weak acidity includes those salts formed between a sulfate ion, a sulfonate ion, a trifluoromethanesulfonate ion, a nitrate ion, a chloride ion, a phosphate ion, etc., and a cation except for a strong basic cation such as alkali metal ions. Specific examples of the cation include transition metal ions, a zinc ion and a magnesium ion. Among these cations, for example, from the viewpoint of enhancing a yield of the glycidol, preferred are a zinc ion, a magnesium ion and a manganese ion. Therefore, sodium sulfate (salt between a strong acid and a strong base) and ammonium carbonate (salt between a weak acid and a weak base) are excluded from the salt having a weak acidity as used in the present invention.

The salt having a weak acidity used in the present invention is preferably a sulfate, a sulfonate or a trifluoromethanesulfonate from the viewpoint of enhancing a yield of the glycidol. Among these salts, preferred are the salts containing at least one cation selected from the group consisting of a zinc ion, magnesium ion and a manganese ion.

The method of reducing the content of the salt having a weak acidity in the glycerol carbonate as used in the present invention is not particularly limited. As such a method for reducing the content of the salt having a weak acidity in the glycerol carbonate, there may be used, for example, a method of subjecting the glycerol carbonate to distillation, a method of neutralizing the salt having a weak acidity in the glycerol carbonate with an alkali, a method of subjecting the glycerol carbonate to adsorption treatment using an adsorbent to remove the salt having a weak acidity therefrom, a method of subjecting the glycerol carbonate to reprecipitation/filtration to remove the salt having a weak acidity therefrom, etc. Among these methods, from the viewpoint of a high yield of the glycidol, the methods using distillation, neutralisation and adsorption treatment are preferably used in the present invention.

In the method of reducing the content of the salt having a weak acidity in the glycerol carbonate by distillation, the distillation procedure may be performed by known distillation methods. Examples of the method used for the distillation procedure include evaporation, continuous evaporation, batch-type simple distillation, continuous-type simple distillation, batch type rectification, continuous-type rectification and molecular distillation. These distillation methods may be used alone or in combination of any two or more thereof. The apparatus used for the distillation procedure is not particularly limited and may be any of ordinarily used distillation apparatuses. The distillation conditions may also be appropriately determined depending upon the salts to be reduced, etc.

In the method of reducing the content of the salt having a weak acidity in the glycerol carbonate by neutralizing the salt with an alkali, a suitable alkali agent may be used depending upon the kind of the salt having a weak acidity. Specific examples of the alkali agent include sodium hydroxide, potassium hydroxide and sodium hydrogencarbonate. The method for performing the neutralization treatment is not particularly limited. For example, the neutralization treatment may be performed by such a method of allowing an excessive amount of the alkali to exist together with the glycerol carbonate. In the method, the neutralization efficiency may be optionally enhanced by stirring or heating. In addition, when any precipitate is formed, any post-treatments such as filtration may be conducted to separate and remove the precipitate from the aimed product.

Also, in the method of reducing the content of the salt having a weak acidity in the glycerol carbonate by the adsorption treatment using an adsorbent, as the adsorbent, there may be used a cation adsorbent such as an organic adsorbent, e.g., strong acid cation exchange resins and weak acid cation exchange resins, and an inorganic adsorbent, e.g., hydrotalcite. The method of performing the adsorption treatment is not particularly limited. For example, the adsorption treatment may be performed by allowing the glycerol carbonate to exist together with the above adsorbent. In the method, the adsorption efficiency may be optionally enhanced by stirring or heating. In addition, any post-treatments such as filtration may be conducted to separate and remove the adsorbent from the aimed product.

In any of the above methods using the distillation, neutralization and adsorption treatments, the treatment conditions may be appropriately determined to control the content of the salt having a weak acidity in the glycerol carbonate to the below-mentioned range.

The glycerol carbonate is subjected to the step (1) of reducing the content of the salt having a weak acidity therein, so that the resulting glycerol carbonate which is thus previously treated to reduce the content of the salt having a weak acidity therein can be suitably used as a raw material for the step (2), In addition, the step (1) may also be performed during the reaction of the step (2) by conducting the reaction while removing the salt having a weak acidity upon production of the glycidol in the step (2).

The salt having a weak acidity which is contained in the glycerol carbonate varies depending upon, for example, the catalyst used upon producing the glycerol carbonate. As the catalyst, there may be used at least one salt selected from the group consisting of sulfates and salts of a sulfate and a decomposed product of urea. Specific examples of the salt as the catalyst include salts having a weak acidify such as zinc sulfate and magnesium sulfate. Meanwhile, for example, when zinc sulfate is used as the catalyst, it is intended that the salt as the catalyst also include, in addition to zinc sulfate itself, salts of zinc sulfate and a decomposed product of urea such as ammonium sulfate and ammonium hydrogensulfate, and composite salts of zinc sulfate and ammonia. The process of the present invention can be suitably applied to removal of the salts having a weak acidity which are produced by using the above catalyst upon producing the glycerol carbonate.

From the viewpoint of enhancing a yield of the glycidol upon the reaction, it is required that the content of the salt having a weak acidity in the glycerol carbonate used as a raw material in the step (2) is reduced to 1500 ppm by mass or less. The content of the salt having a weak acidity in the glycerol carbonate is reduced until it reaches preferably 1000 ppm by mass or less, more preferably 500 ppm by mass or less, still more preferably 300 ppm by mass or less and further still more preferably from 1 to 200 ppm by mass. In particular, when the salt to be reduced is a sulfate, the content of the sulfate in the glycerol carbonate is reduced until it reaches preferably 500 ppm by mass or less, more preferably 300 ppm by mass or less and still more preferably from 1 to 200 ppm by mass.

Step (2)

In the step (2), glycidol is produced from glycerol carbonate. The glycerol carbonate used in the step (2) is preferably the glycerol carbonate which is subjected to the step (1) to reduce the content of the salt having a weak acidity therein to the above-mentioned range. More specifically, as the glycerol carbonate used as a raw material in the step (2), there may be used not only the glycerol carbonate which is previously treated to reduce the content of the salt having a weak acidity therein, but also glycerol carbonate which is not subjected to any treatment for reducing the content of the salt having a weak acidity therein. If the glycerol carbonate which is not subjected to any treatment for reducing the content of the salt having a weak acidity therein is used in the step (2), the content of the salt having a weak acidity in the glycerol carbonate may be reduced during the reaction of the step (2).

The reaction used in the step (2) for producing the glycidol may be a known reaction such as ordinary decarboxylation reaction. The reaction may be carried out without using any catalyst. In order to allow the reaction to proceed in a facilitated manner, a neutral salt, e.g., an alkali metal salt such as sodium sulfate and sodium chloride and/or an alkali earth metal salt, etc., is preferably used as the catalyst. In this case, the amount of the catalyst used is usually from 0.1 to 10 mol % and preferably from 1 to 7 mol % on the basis of the glycerol carbonate.

The temperature and pressure used in the reaction of the step (2) are not particularly limited. However, the reaction of the step (2) is suitably carried out at a temperature of preferably from 100 to 300° C. and more preferably from 125 to 275° C. under a pressure of preferably from 0.1 to 500 kPa and more preferably from 0.3 to 200 kPa. If the treatment for reducing the content of the salt having a weak acidity in the glycerol carbonate is conducted in the step (2), the treatment conditions may be controlled to the same conditions as described above.

The glycerol carbonate used in the present invention may include those produced by any of the method using phosgene, the method of subjecting dimethyl carbonate, ethylene carbonate, propylene carbonate, etc., and glycerol to exchange reaction therebetween, the method of obtaining the glycerol carbonate from glycerol and urea, etc. Among these glycerol carbonates, from the viewpoint of producing the glycerol carbonate in a simple and facilitated manner at low costs, preferred is the glycerol carbonate obtained from glycerol and urea. In this case, when using the glycerol carbonate produced from glycerol and urea in the presence of the above catalyst, the effects of the present invention can be more remarkably exhibited.

In the following, the process for producing the glycerol carbonate from glycerol and urea is briefly explained.

In the production process, relatively inexpensive glycerol and urea are used as raw materials, and the glycerol carbonate can be readily produced only by reacting these raw materials with each other. The ratio between glycerol and urea charged in the production process is suitably controlled such that urea is used in an amount of from 0.2 to 2.0 mol and preferably from 0.5 to 1.5 mol per 1 mol of glycerol.

The above reaction may be conducted even without using any catalyst. However, the reaction is preferably conducted in the presence of a Lewis acid catalyst such as zinc sulfate and magnesium sulfate in order to allow the reaction to proceed in a facilitated manner. In this case, the amount of the catalyst used in the reaction is preferably from 0.001 to 10 mol % on the basis of glycerol.

Since the above catalyst corresponds to the salt having a weak acidity, the reaction systems using the catalyst provide preferred embodiments in which the effects of the present invention are remarkably exhibited when applied thereto.

In the above production process, from the viewpoint of enhancing a yield of the glycerol carbonate, glycerol used as the raw material is preferably fully dehydrated, and the reaction is preferably conducted using a dehydrating agent such as magnesium sulfate.

In addition, from the viewpoint of efficiently removing ammonia generated in the reaction, there is preferably used a method of flowing nitrogen through the reaction system or a method of conducting the reaction under reduced pressure. The amount of the nitrogen flowing through the reaction system is not particularly limited as long as ammonia and excessive water are sufficiently removed therefrom. The nitrogen is preferably introduced into the glycerol liquid phase. When the reaction is conducted under reduced pressure, the reduced pressure is preferably in the range of from 1 to 200 kPa. The reaction temperature is preferably from 80 to 160° C. and more preferably from 100 to 160° C.

In the present invention, the thus obtained glycerol carbonate is suitably used in the step (1).

EXAMPLES

The present invention is described in more detail below by referring to the following Examples, etc. However, the following Examples are only illustrative and not intended to limit the invention thereto.

Reference Example 1

Synthesis of Glycerol Carbonate

A 300 mL four-necked flask was charged with 102 g (1.1 mol) of glycerol, 61 g (1 mol) of urea and 3.6 g (0.02 mol) of zinc sulfate monohydrate. An inside pressure of the flask was reduced to 2.7 kPa, and the mixture in the flask was gradually heated to 150° C. Since ammonia was generated as the reaction proceeded, the reaction was conducted while neutralizing the reaction solution with phosphoric acid. The obtained reaction solution was aged at a temperature of from 150 to 160° C. for 2 h, and then cooled to remove insoluble components therefrom by filtration, thereby obtaining 110 g of glycerol carbonate. As a result, it was confirmed that the content of a salt having a weak acidity hi the thus obtained glycerol carbonate was 12000 ppm by mass. Meanwhile, the content of the salt having a weak acidity in the obtained glycerol carbonate was determined by measuring the amount of a sulfuric ion as detected by ion chromatography. This determination method is similarly applied to the subsequent descriptions.

Example 1

A 300 mL four-necked flask was charged with 80 g of the glycerol carbonate obtained in Reference Example 1, and the glycerol carbonate was subjected to distillation at a temperature of from 150 to 170° C. under a vacuum degree of from 0.13 to 0.27 kPa, thereby obtaining 58 g of glycerol carbonate (as a distillation product). It was confirmed that the content of a salt having a weak acidity in the resulting glycerol carbonate was 100 ppm by mass.

Successively, 40 g of the glycerol carbonate as the distillation product and 4 g of anhydrous sodium sulfate were charged into a four-necked flask and gradually heated to 180° C. under a pressure of 0.4 kPa to allow glycidol to be distilled off. The reaction solution in the flask was continuously stirred at 180° C. for 3 h, thereby obtaining 16 g of glycidol (isolation yield: 62%),

Example 2

A 300 mL four-necked flask was charged with 40 g of the glycerol carbonate obtained in Reference Example 1 and 4 g of sodium hydrogencarbonate, and the mixture in the flask was gradually heated to 155° C. under a pressure of 0.4 kPa to allow glycidol to be distilled off therefrom. The reaction mixture in the flask were continuously stirred at 155° C. for 3 h, thereby obtaining 9.8 g of glycidol (isolation yield: 39%).

Example 3

A 300 mL four-necked flask was charged with 40 g of the glycerol carbonate obtained in Reference Example 1 and 4 g of hydrotalcite as an acid adsorbent (tradename "KYOWARD 500" available from Kyowa Chemical Co., Ltd.), and the mixture in the flask was gradually heated to 160° C. under a pressure of 0.4 kPa to allow glycidol to be distilled off therefrom. The reaction mixture in the flask was continuously stirred at 160° C. for 4 h, thereby obtaining 11 g of glycidol (isolation yield: 45%).

Example 4

A 300 mL four-necked flask was charged with 4 g of anhydrous sodium sulfate which was then heated to 200° C. under a pressure of 0.4 kPa. Thereafter, 40.0 g of glycerol carbonate containing no salt having a weak acidity (guaranteed reagent available from Tokyo Kasei Co., Ltd.) was dropped into the flask over 1 h. While allowing the respective components in the flask to react with each other, glycidol distilled off therefrom was recovered. After completion of the dropping, the obtained reaction solution was aged at 200° C. for 1 h, thereby finally obtaining 19.8 g of glycidol (isolation yield: 79%),

Example 5

A 300 mL four-necked flask was charged with 4 g of anhydrous sodium sulfate and 0.01 g of anhydrous zinc sulfate (250 ppm based on glycerol carbonate), and the mixture in the flask was heated to 200° C. under a pressure of 0.4 kPa. Thereafter, 40.0 g of glycerol carbonate containing no salt having a weak acidity (guaranteed reagent available from Tokyo Kasei Co., Ltd.) was dropped into the flask over 1 h. While allowing the respective components in the flask to react with each other, glycidol distilled off therefrom was recovered. After completion of the dropping, the obtained reaction solution was aged at 200° C. for 1 h, thereby finally obtaining 16.6 g of glycidol (isolation yield: 66%).

Comparative Example 1

A 300 mL four-necked flask was charged with 35 g of the glycerol carbonate obtained in Reference Example 1 and 3.5 g of anhydrous sodium sulfate, and the mixture in the flask was gradually heated to 180° C. under a pressure of 0.4 kPa. Although the mixture in the flask was continuously stirred for 3 h, no glycidol was obtained. Thereafter, the mixture in the flask was heated to 200° C. and further stirred for 2 h. However, no glycidol was obtained (isolation yield: 0%).

INDUSTRIAL APPLICABILITY

According to the production process of the present invention, glycidol can be produced with a high yield. The thus obtained glycidol can be suitably used for production of polyglycerol, polyglycerol fatty acid esters, etc.

The invention claimed is:

1. A process for producing glycidol, comprising the steps of:
   (1) reducing a content of a salt having a weak acidity in glycerol carbonate to 1500 ppm by mass or less; and
   (2) obtaining the glycidol from the glycerol carbonate.

2. The process according to claim 1, wherein the glycerol carbonate is obtained from glycerol and urea in the presence of an acid catalyst.

3. The process according to claim 1 or 2, wherein the glycerol carbonate is subjected to distillation to reduce the content of the salt having a weak acidity therein.

4. A process for producing glycidol, comprising the steps of:
   (1) reducing a content of a salt having a weak acidity in glycerol carbonate to 1500 ppm by mass or less; and
   (2) obtaining the glycidol from the glycerol carbonate;
   wherein the glycerol carbonate is subjected to adsorption treatment to reduce the content of the salt having a weak acidity therein.

5. The process according to claim 1, wherein the content of the salt having a weak acidity in the glycerol carbonate used in the step (2) is 1000 ppm by mass or less.

6. A process for producing glycidol, comprising the steps of:
   (1) reducing a content of a salt having a weak acidity in glycerol carbonate to 1500 ppm by mass or less; and
   (2) obtaining the glycidol from the glycerol carbonate;
   wherein the salt having a weak acidity is a sulfate, a sulfonate or a trifluoromethanesulfonate which comprises at least one cation selected from the group consisting of a zinc ion, a magnesium ion and a manganese ion.

* * * * *